United States Patent [19]

Finn

[11] Patent Number: 5,370,701
[45] Date of Patent: Dec. 6, 1994

[54] ROTATING/SLIDING CONTRAINED PROSTHETIC KNEE

[75] Inventor: Henry A. Finn, Chicago, Ill.

[73] Assignee: Arch Development Corporation, Chicago, Ill.

[21] Appl. No.: 987,106

[22] Filed: Dec. 7, 1992

Related U.S. Application Data

[63] Continuation of Ser. No. 590,255, Sep. 28, 1990, abandoned.

[51] Int. Cl.$^5$ ............................................... A61F 2/38
[52] U.S. Cl. ................................................... 623/20
[58] Field of Search ................... 623/16, 18, 19, 22, 623/20

[56] References Cited

U.S. PATENT DOCUMENTS

| | | |
|---|---|---|
| 4,112,522 | 9/1978 | Dadurian et al. ............ 623/20 |
| 4,136,405 | 1/1979 | Pastrick et al. ............. 623/20 |
| 4,301,553 | 11/1981 | Noiles ......................... 623/20 |
| 4,462,120 | 7/1984 | Rambert et al. ............. 623/20 |
| 4,790,853 | 12/1988 | Engelbrecht et al. ........ 623/20 |
| 4,936,853 | 6/1990 | Fabian et al. ................ 623/20 |

FOREIGN PATENT DOCUMENTS

| | | | |
|---|---|---|---|
| 2566657 | 1/1986 | France | 623/20 |
| 2601873 | 1/1988 | France | 623/20 |

*Primary Examiner*—David Isabella
*Attorney, Agent, or Firm*—McDermott, Will & Emery

[57] ABSTRACT

A constrained prosthetic knee for surgical replacement of a dysfunctional knee includes a tibial platform, a movable bearing element, a hinge portion, and a femoral component.

In one embodiment of the invention, the femoral component is typically constructed of a cobalt-chromium or titanium alloy and includes an upward extension for securing the femoral component to the femur. The femoral component, in this embodiment, includes a convex curve which rotatably and/or slidably engages the movable bearing, typically constructed of high molecular weight polyethylene. The superior surface of the bearing element is designed to congruently slidably engage the inferior surface of the curved portion of the femoral component. The inferior surface of the femoral component is generally convex with a radius of curvature matching the superior surface of the bearing element. The inferior surface of the femoral component may have more than one radii of curvature at different points along the convex surface.

The superior surface of the tibial platform is generally flat and may include one or more protrusions for controlling the movement of the bearing element as it slides on the superior surface of the tibial platform. The hinge portion of the prosthetic device includes a lateral hinge pin and a yoke which rotatably mounts the femoral component on the tibial platform and provides two planes of rotation. The tibial platform includes a depending stem for securing the tibial portion to the tibia. A coaxial superior-inferior shaft within the tibial stem supports the yoke to define the plane of rotation of the hinge portion relative to the tibial platform.

5 Claims, 4 Drawing Sheets

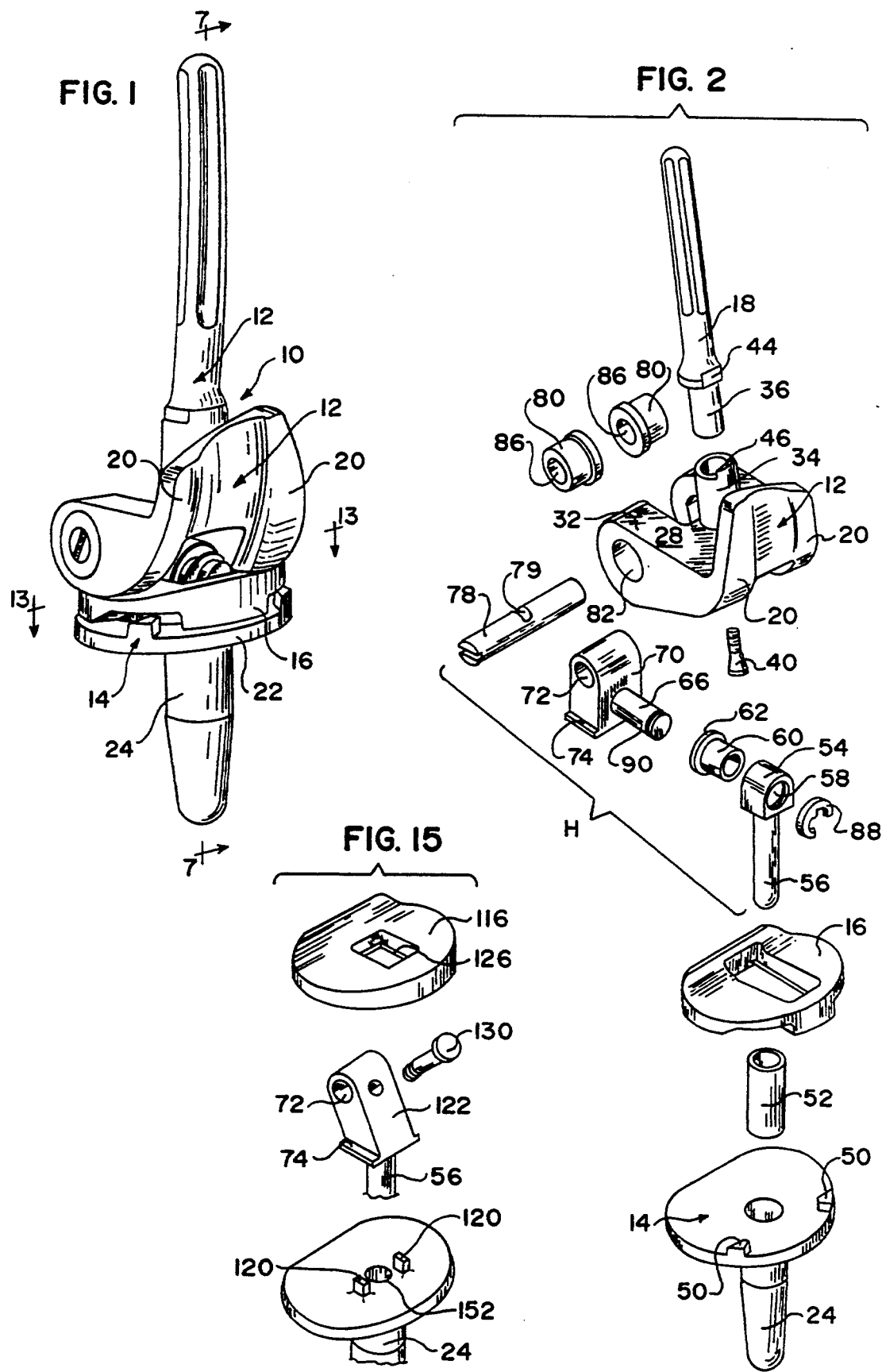

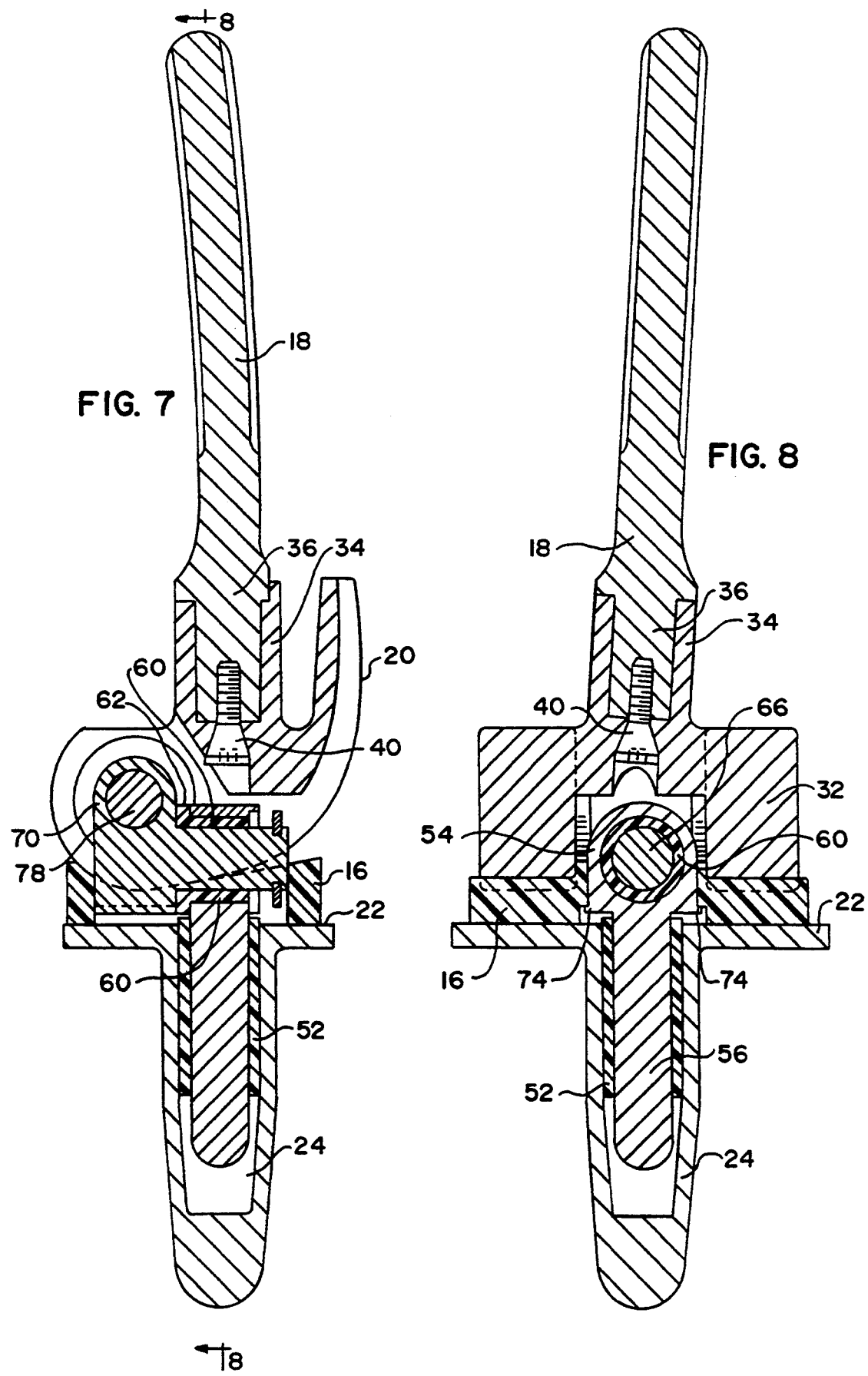

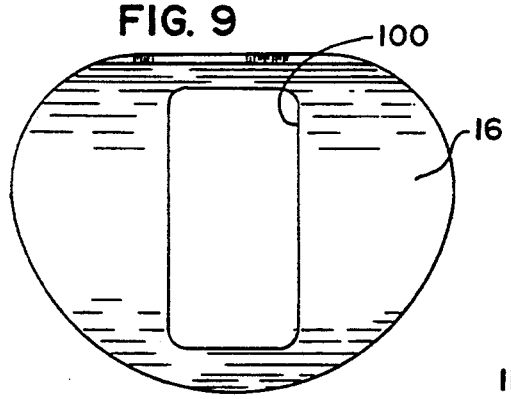
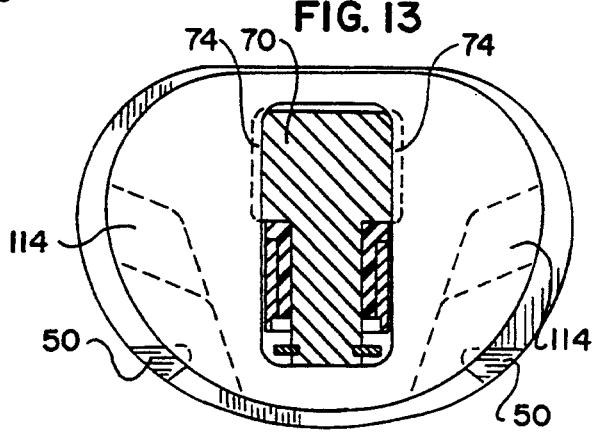
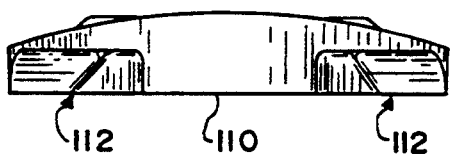
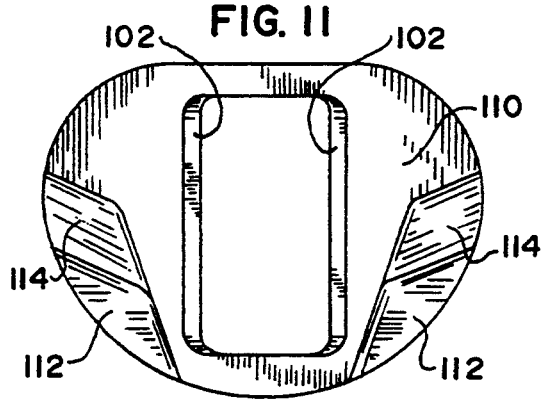
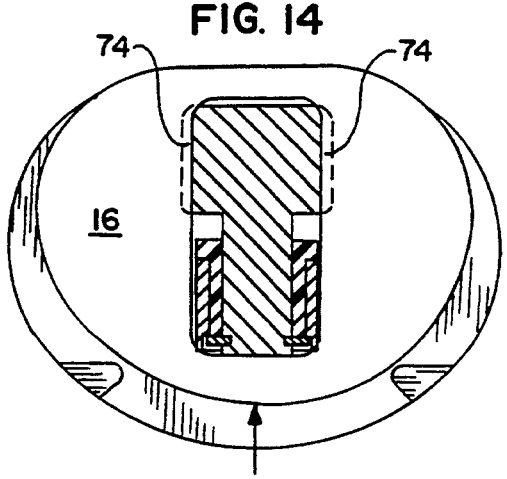
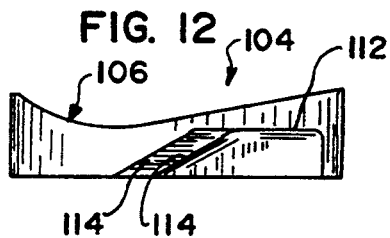

ROTATING/SLIDING CONTRAINED PROSTHETIC KNEE

CROSS REFERENCE TO RELATED APPLICATION

This application is a continuation of U.S. patent application Ser. No. 590,255, filed Sep. 28, 1990, now abandoned.

BACKGROUND OF THE INVENTION

1. Field of the Invention

This invention relates to prosthetic joints generally, and more particularly to a rotating/sliding constrained prosthetic knee replacement for a dysfunctional knee.

2. Prior Art

Referring now to prior art knee endoprostheses, there are basically two types of prosthetic replacement knees known generally as constrained and unconstrained knees. An example of a prior art constrained or hinged knee is shown in U.S. Pat. No. 4,219,893 to Douglas G. Noiles. An embodiment of the Noiles invention is manufactured and sold by Howmedica, Inc. of Rutherford, N.J. An example of an unconstrained or floating meniscal bearing knee is disclosed in Buechel et al U.S. Pat. No. 4,340,978. An embodiment of the Buechle invention is manufactured and sold by Zimmer, Inc. of Warsaw, Ind. Preferably, the bearing elements of both types of knees are manufactured with high density polyethylene such as that disclosed in Zachariades U.S. Pat. No. 4,587,163 developed by Polteco Inc. of Alameda, Calif. because of its superior wear resistant characteristics. Both classes of prior art prosthetic knees have had problems often resulting in failures requiring additional surgery and repair or reconstruction.

In particular, pre-existing constrained knees have often resulted in early failure as a result of hinge constrainment. The degree of rotation was limited to either only one plane or a very small arc causing a loosening and failure of the connection points between the prosthesis and the tibia or femur. Also, as shown in U.S. Pat. No. 4,219,893, very little flexibility was possible in the shape of the patello-femoral interfaces because of the requirement to maintain congruent patello-femoral contact over the range of motion of the knee. As a result, patello-femoral tracking problems became commonplace.

It was necessary to use a large circumference when resurfacing allografts resulting in problems with soft tissue necrosis and/or patello-femoral tracking problems as described above. Furthermore, most implants were custom devices since they had to be specially made to fit a particular patient's size and thus required excess manufacturing time and unnecessary delays. None of the prior art devices of either class were capable of being made in "modular" form, which simplified procurement and inventory problems associated with custom devices.

An additional, significant problem with prior art constrained knees results from the fact that the range of motion prevents the normal A-P movement of the inferior end of the femur relative to the superior end of the tibia. This "sliding" movement is necessary in order to maintain the full range of motion desired in a prosthetic device and to approximate normal human kinematics.

Both constrained and unconstrained prosthetic knees suffer from some of the same deficiencies but also include additional problems. In particular, it has been shown that such prior art prostheses have poorly designed patello-femoral interfaces in that they do not provide reasonable congruent patello-femoral contact or sliding engagement over any appreciable range of knee motion. These prior art prostheses typically produce contact stresses which result in yielding and fatigue of the plastic bearing surface typically present in such prostheses. This result is caused by the fact that the bearing surface of the femoral component, over which the patella prosthesis must pass, generally has several regions or segments of differing shape. For example, there is typically a fairly long, singly curved segment blending into a first doubly curved segment blending again into a second, and different, doubly curved segment. Thus, when the patella prosthesis goes through its excursion over the femoral articular flange, the patella prosthesis undergoes a variety of contact conditions, namely, substantial portions of line contact, portions of point contact, and perhaps limited portions of area or congruent area contact. As is known, line contact and point contact conditions generally produce high contact stresses which produce yielding and possible wear of the polyethylene portion of the prostheses. Hence, the extended wear life needed for successful prosthetic implantation is not realized.

Referring next to typical prior art tibial-femoral knee prostheses, prostheses which allow axial rotation and A-P motion in addition to flexion-extension motion have incongruent contact (usually theoretical point-contact) between the femoral and tibial bearing surfaces, have been found to produce excessive contact stresses leading to deformation and/or early wear and undesirably short prosthetic life. Also, wear products have been shown to produce undesirable tissue reactions which may contribute to loosening of the prosthetic components.

Those prior art knee prostheses which do provide congruent or area bearing contact fail to provide the needed axial rotation, or when cruciates are present the needed anterior-posterior motion. This lack of axial rotation and anterior-posterior motion has been found clinically and experimentally to result in deformation and loosening of the tibial components, and such prostheses now appear to be falling into disuse.

Current prostheses of the dislocatable cruciate retaining type, such as the Geomedic knee replacement shown in U.S. Pat. No. 3,728,742 to Averill et al., that produce area contact provide only one axis of rotation relative to the femur for the flexion-extension motion. Normal flexion-extension is, however, characterized by apolycentric flexion-extension motion where rotation relative to the femur occurs about many axes. This polycentric motion, which results from the action of the cruciate ligaments and condylar shape, allows for more efficient utilization of muscle forces by providing a posterior shift of the axis when effective quadriceps action is important and an anterior shift when hamstrings effectiveness is important. Furthermore, in the human knee it is this action and the A-P shift, and the shape of the posterior condyles, which influence this motion so as to allow full flexion capability for the knee. Failure to provide appropriate knee geometry inhibits, when cruciate ligaments are present, this natural motion and thus tends to restrict muscle effectiveness and inhibit flexion. These restrictions tend to increase both loading on the prosthesis (which increases wear or likelihood of deformation or breakage) and loading between prosthesis and bone (which increases the possibility of component loosening).

It has been found that loosening problems result from the direct attachment of plastic prosthetic components to bone through the use of relatively brittle cement that is weak in tension. Specifically, it has been demonstrated that even relatively thick plastic components when loaded in a normal fashion produce undesirable tensile stresses in the acrylic cement commonly used to secure such plastic components to bone. Such loading tends to produce bending of the plastic component which causes the ends of the plastic component to lift away from the bone, thereby subjecting the bone-cement attachment to tension. As is known, cement has very poor tensile fatigue properties. The bone to which the plastic prosthesis is cemented also appears to be adversely affected by tensile loads. Accordingly, these combined effects contribute substantially to prosthetic loosening problems and, specifically, it has been noted where clinical failure due to loosening occurs in a knee prosthesis that is almost always the plastic prosthesis component which loosens.

Another prior art prosthesis problem exists with regard to knee endoprostheses for implantation in those cases wherein the cruciate ligaments are functionally absent but where the collateral ligaments are functional or at least reconstructable. In the absence of cruciate ligaments, the prosthetic replacement must provide anterior-posterior knee joint stability so as to replace that stability otherwise provided by the cruciates. Until recently most such cases were treated by a constrained type knee prosthesis which may suffer from the loosening problems described above caused by the stresses described above. Necrosis of the bone, caused by altered mechanical bone stresses, is also a problem with the prior art constrained knee prostheses.

Where the cruciate ligaments are present, most surgeons would prefer their retention, since they provide important internal stabilizers and, together with the condylar geometry of the femur and tibia, control the rotation axis of the knee. Furthermore, these ligaments provide anterior-posterior stability. Thus, it is desirable to reserve the cruciate ligaments, even though reasonable stability can be provided by a properly designed full platform type prosthesis.

In addition, the action of the cruciate ligaments produces a shift in the rotation axis of the knee which may result in more efficient muscle utilization. Thus, preservation of these structures may provide better physiological function after knee replacement.

It is not, however, clear that the physiological advantages gained in retaining the cruciates outweigh the disadvantages of the design compromises, such as increased bearing surface incongruency and reduced tibial prosthesis bearing area, required to retain these ligaments. Thus, the desirability of retaining the cruciate ligaments in the cases of unconstrained knee replacement is not well established.

A recent unconstrained knee concept, the New Jersey knee, appears to provide a partial solution to the problem of overconstraint while maintaining congruency by the use of mensical floating elements. Unfortunately, this knee suffers from several design problems which appear to limit its usefulness.

The present invention, the Finn Knee, utilizes new concepts combined in an improved low profile design in order to avoid some of the anticipated difficulties of the prior art design.

SUMMARY OF INVENTION

The present invention is directed to an improved prosthesis for the replacement of all or a portion of a dysfunctional human knee joint.

An object of the present invention is to provide a constrained knee prosthesis with a smaller femoral component in both the anterior/posterior and medial/lateral directions.

A further object of the present invention is to provide a knee prosthesis which facilitates rotation about one or more axes in the presence of congruency and rigidity of the bearing surfaces.

An object of the present invention is to provide a knee prosthesis in which A-P sliding of the bearing element with knee flexion is similar to the normal anatomical shift in the center of the area of contact between femoral and tibial condyles.

A further object of the present invention is to provide a knee prosthesis with improved medial-lateral stability, substantially unaffected by axial rotation or anterior-posterior (A-P) shift of the bearing element.

A further object of the present invention is to provide a modular knee prosthesis utilizing Morse cones to allow easy use with or without allografts.

A further object of the present invention is to provide a constrained knee prosthesis having extramedullary porous ingrowth capability with the host or allograft bone.

A further object of the present invention is to provide a constrained knee prosthesis where the femoral component may articulate in extremely close proximity with the tibia to eliminate patella baha problems.

A further object of the present invention is to provide a knee prosthesis which eliminates the possibility of tipping or dislocation of the bearing insert.

A further object of the present invention is to provide a knee prosthesis which allows full flexion of the reconstructed knee.

A further object of the present invention is to provide a knee prosthesis having reduced tendency toward loosening and collapse, as compared with prior-art floating bearing insert type knee prostheses.

BRIEF DESCRIPTION OF THE DRAWINGS

A complete understanding of the invention may be obtained from the detailed description which follows, together with the accompanying drawings, wherein:

FIG. 1 is a perspective view of the constrained/sliding prosthetic knee of the present invention;

FIG. 2 is an exploded perspective view of the constrained/sliding prosthetic knee of the present invention;

FIG. 7 is a vertical section of the constrained/sliding prosthetic knee of the present invention taken generally along line 7—7 of FIG. 1;

FIG. 8 is a vertical section of the constrained/sliding prosthetic knee of the present invention taken generally along line 8—8 of FIG. 7;

FIG. 9 is a top plan of the bearing element shown in FIG. 2;

FIG. 10 is a front elevational view of the bearing element shown in FIG. 2;

FIG. 11 is a bottom plan view of the bearing element shown in FIG. 2;

FIG. 12 is a side elevational view of the bearing element shown in FIG. 2;

FIG. 13 is a horizontal section of the assembled constrained/sliding prosthetic knee of the present invention taken generally along line 13—13 of FIG. 1;

FIG. 14 is a horizontal section similar to FIG. 13 showing the bearing element in its rearwardmost position;

FIG. 15 is an alternate embodiment of the modular form of the inferior portion of the femoral component of the present invention; and FIG. 16 is an alternate embodiment of a constrained knee made in accordance with the present invention.

BRIEF DESCRIPTION OF THE PREFERRED EMBODIMENT

Figure 3:
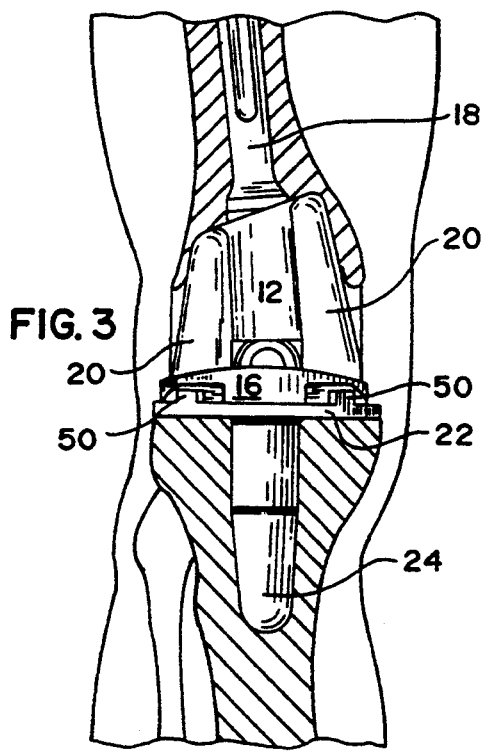
FIG. 3 is a front elevational view of the constrained/sliding prosthetic knee of the present invention.

Referring now in particular to FIG. 1, the rotating/sliding constrained knee, generally designated 10, is shown in perspective view to include a femoral component 12, a tibial component 14, a bearing element 16, and a hinge portion H. The femoral component 12 includes a first fixation means including an upwardly extending stem 18 and a first bearing surface including a pair of condyles 20 at its inferior end for engagement with the bearing element 16.

Preferably, the bearing element 16 is constructed of a tough, wear-resistant, resilient material such as high density polyethylene. The remaining elements of the prosthetic knee are metallic and preferably manufactured of a cobalt-chromium alloy or titanium material approved for use in prosthetic devices.

The tibial portion includes a second fixation means in the form of a hollow stem portion 24 for securing the tibial portion to the tibia. A second bearing surface on the second fixation means includes a generally flat platform 22. The lower portion of the stem 24 and the implantable stem portion 18 of the tibial portion include a surface adapted for extramedullary porous ingrowth to secure the prosthetic device within the tibia and femur, respectively, of the host or allograft bone of the patient.

Referring more particularly to FIG. 2, the femoral component 12 includes a pair of condyles, which are highly polished to reduce friction, formed on the base portion 28 of the femoral component 12. The base portion includes a pair of posteriorly extending lobes 32 for connection to the hinge element H as described hereinafter. An upstanding connector shaft 34 is angularly mounted on the superior surface of the base 28 for receiving a similarly sized depending stud 36 on the inferior end of the stem 18. The stem 18 is secured to the base 28 by a bolt 40 which extends through the base to mating threads within the post 36. A flat 44 engages an upstanding cordal segment 46 on the post 34 to maintain proper alignment between the stem and the base upon assembly. Different shapes and lengths of the stem portion can be used with a mating base portion to "customize" the knee for a particular patient.

Referring now to the lower portion of FIG. 2, the tibial platform portion includes the platform 14 and the depending stem 24. The platform is provided with a pair of triangular shaped protrusions or stops 50 for limiting the rotation of the bearing as will be described in greater detail hereinafter. As previously described, the tibial stem portion 24 is hollow and permits the insertion of a bushing 52 for receiving the hinge element H as described below.

The hinge portion is generally designated as the elements enclosed by the bracket H in FIG. 2. The hinge element includes several individual components which are assembled to secure the femoral component in relation to the tibial platform while permitting movement in three planes. In particular, the hinge element includes a yoke 54 which includes a depending bearing shaft 56. The shaft 56 fits within the bushing 52 to provide rotation about the vertical or S-I (superior-inferior) axis. The yoke 54 includes a generally centrally located aperture 58 which receives a bushing 60 on its posterior side. The bushing 60 includes a flange 62 at the posterior end and receives anteriorly extending slidable shaft 66. The shaft 66 is mounted to a posterior yoke 70 which provides an axis of rotation in the medial-lateral plane. The yoke 70, on its interior surface, carries a pair of flanges 74 which extend in the medial-lateral (M-L) direction and engage the lower surface of the bearing element 16 as described in detail hereinafter. A hinge pin or shaft 78 is provided to connect the posterior yoke 70 to the lobes 32 of the femoral component. A pair of suitable bushings 80 are sized to fit within a pair of apertures 82 in the lobes 32 of the femoral component and have internal diameters 86 to receive the hinge pin 78. The anterior shaft 66 of the yoke 70 extends through the bushing 60 and the anterior yoke 54 and is captured by a C-ring 88 which engages an undercut 90 in the sliding shaft 66 as can be seen more easily in FIG. 7. The distance between the undercut 90 and the anterior surface of the yoke 70 is slightly larger than the A-P length of the bushing 60 to permit the shaft 66 to move in the A-P direction. Thus, when assembled, the hinge element 18 permits the hinge pin 78 and thus the femoral component to move in the A-P direction through a distance of approximately 0.18 to 0.30 inches. This construction of the hinged, or constrained, rotating/sliding prosthesis permits A-P shifting of the femoral component during knee flexion which is very similar to the normal anatomical shift in the center of the area of the contact between femoral and tibial condyles.

In the embodiment of the present invention which provides the A-P shift of the femoral component, described above, the tibial bearing 16 provides support for the weight of the patient with a very durable, but resilient element.

Referring to FIG. 9, the bearing element 16 is generally egg-shaped with a flattened posterior surface when viewed from the top as in FIG. 9. The overall circumference including the A-P dimension and M-L dimension are substantially smaller than previously used in prosthetic knee replacements. The bearing includes a generally rectangular centrally located aperture 100 having its longer length generally in the A-P direction. The aperture 100 is generally sized to contact the medial-lateral surfaces of the posterior yoke 70 as shown in the sectional view of FIG. 13 with the lower extending flanges 74 sliding within a groove 102 shown on the bottom of the rectangular opening in FIG. 11. The upper surface of the bearing element, generally designated 104 in FIG. 12, includes an arcuate surface which is generally flat in the anterior region, reaching its lowest point about 70% toward the posterior end and then curving upwardly as shown. The rearward and lowermost curved portions 106 are designed to be congruent with the condyles 20 to provide maximum surface contact as shown in FIG. 7. The lower generally flat surface 110 of the bearing element slidably engages the superior surface of the tibial platform and as can be seen in FIG. 11, provides full surface area contact through a substantial portion of the bearing element, particularly under the portion in contact with the condyles.

A pair of undercuts 112 and angled surfaces and 114 on the inferior surface of the bearing element near the anterior edge permit the bearing to both rotate about a vertical (S-I) axis and slide in an A-P direction while avoiding the protrusions 50 on the top of the tibial platform. These protrusions 50 serve to engage the surfaces 114 of the undercuts 112 to limit the rotation of the bearing element and thus the femoral component 12. As seen particularly in FIG. 13, with the bearing element and hinge pin 78 in its most forward position, the protrusions 50 are partially encapsulated by the undercut portions 112 of the bearing portion 16. If rotation occurs around the vertical axis, the undercut angular surfaces 114 on either side of the bearing will engage the protrusions 50 and thereby limit rotation.

Figure 4:
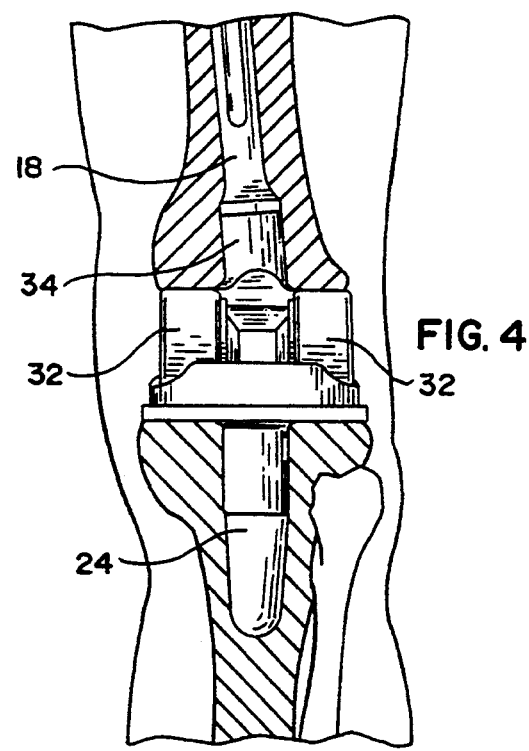
FIG. 4 is a rear elevational view of the constrained/sliding prosthetic knee of the present invention.
Figure 5:
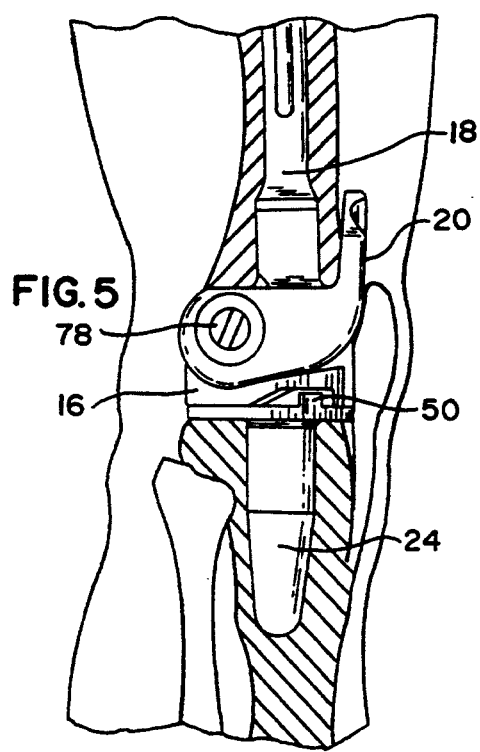
FIG. 5 is a side elevational view of the constrained/sliding prosthetic knee of the present invention.
Figure 6:
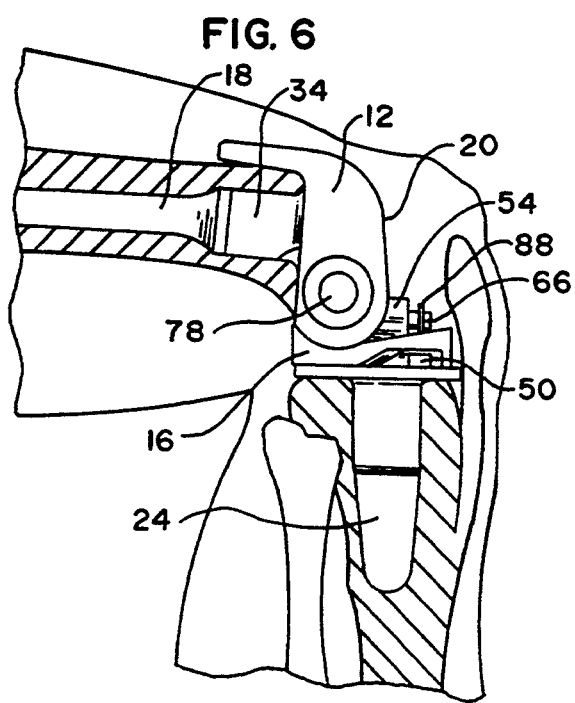
FIG. 6 is another side elevational view of the constrained/sliding prosthetic knee of the present invention in full extension.

Again referring to FIG. 7, while the femoral component is shown in its forwardmost position, in use, when the knee is in its extended position, the femoral component would cause the bearing element 16 to move to its rearwardmost position as shown in FIG. 14. Also, as shown in FIGS. 7 and 8, a posteriorly bowed femoral stem 18 is preferably provided however, the modular design permits the use of several types of straight or segmental replacement stems if desired. In addition, as shown more accurately in FIGS. 3, 4 and 8, the upstanding post 34 on the femoral component base 28 extends inwardly in the superior direction in the manner to accommodate the axis of the femur.

An alternate embodiment of the prosthetic knee is shown generally in FIG. 15 and like numbers are used to identify the same component. FIG. 15 shows the elements used in the non-sliding embodiment of the invention which does not allow the sliding A-P shift of the bearing 14 and femoral component. In some non-sliding situations, because of certain patient characteristics, a physician may decide that additional stability in the A-P direction is necessary because of the damage or other reason. In this embodiment, the bearing 114 has a generally square shaped aperture, and a superior profile similar to that shown in FIG. 12 for the sliding embodiment. In this embodiment, however, the superior surface of the tibial platform is modified to provide a pair of inboard protrusions 120 adjacent a vertical, circular journal 152. The yoke 122 is modified to resemble a canted version of the posterior yoke 70 of the sliding embodiment which is extended upwardly and posteriorly as shown to provide a similar hinge pin aperture 72 which is fixed relative to the vertical shaft portion 56 of the yoke. In this embodiment, again the hinge pin 78 through the aperture 72 supports the femoral component rotating about the M-L axis of the hinge pin 78 and the vertical, S-I axis of the shaft 56 while the weight of the patient is supported by the bearing element 116. A similar groove 126 in the bottom surface of the bearing 116 engages the M-L extensions 74 on the yoke 122. Again, a pair of notches or cutout portions 124 permit rotation of the bearing element 116 through a prescribed degree of rotation. Preferably, a threaded bolt 130 secures the hinge pin 78 against M-L movement by engagement with the notch 79.

The foregoing detailed description has been given for clearness of understanding only and no unnecessary limitations should be understood therefrom as some modifications would be obvious to those skilled in the art.

I claim:

1. An improved prosthetic device for performing the function of a knee joint between the femur and tibia bones of a human, each having a generally longitudinal axis, comprising:

femoral attachment means adapted for attachment to the femur, said femoral attachment means including a stem portion for insertion into the femur and a base portion, said stem being removable from said base, and means to secure the stem to the base;

a pair of depending, convex bearing surfaces on said base portion of said femoral attachment means;

tibial attachment means adapted for attachment to the tibia, said tibial attachment means including a generally hollow, depending stem and a generally flat platform portion;

a planar bearing surface on the platform portion of the tibial attachment means, said planar bearing surface generally at right angles of the longitudinal axis of said tibia;

hinge means for connecting said femoral attachment means to said tibial attachment means for rotation about an axis generally perpendicular to the longitudinal axis of the tibia, said hinge means including a pair of medial-lateral spaced apertures in the base portion of the femoral attachment means, a hinge pin, and a yoke having an aligned, medial-lateral aperture for receiving said hinge pin;

a bearing element between said convex bearing surfaces and said planar bearing surface and having a pair of generally concave surfaces on one side for engaging said convex surfaces and an opposite, generally flat side, mating in congruent bearing relationship with said planar bearing surface; and means for mounting the bearing element on the tibial attachment means to permit rotary and sliding movement between the bearing element and the planar bearing surface, said mounting means including an elongated aperture in the bearing element for engaging the medial-lateral exterior surfaces of said yoke portion of the hinge means to permit translatory movement generally in the anterior-posterior direction and a depending bearing shaft on the yoke for insertion into the hollow stem of the tibial attachment means to permit rotary movement of the yoke;

whereby said bearing element is freely rotatable through a prescribed arc in a plane approximately perpendicular to the longitudinal axis of said tibia and slideable relative to said tibia to permit natural movement between the femur and tibia.

2. A prosthetic device as claimed in claim 1 wherein said mutually congruent thrust bearing surface is a nearly flat surface of revolution.

3. A prosthetic device as claimed in claim 2 further including stop means for limiting the movement of said congruent thrust bearing.

4. A prosthetic device as claimed in claim 3 wherein said stop means limits movement of said congruent thrust bearing to approximately 40°.

5. A prosthetic device as claimed in claim 3 wherein said second fixation means comprises an arcuate flange portion along its periphery and stop means extending from the arcuate flange portion radially inward and said congruent thrust bearing surface, of said intermediate load bearing member comprises abutment means for engaging said stop means.

* * * * *